United States Patent [19]

Smith et al.

[11] Patent Number: 4,986,834
[45] Date of Patent: Jan. 22, 1991

[54] LOAD SHARING FEMORAL HIP IMPLANT

[75] Inventors: Todd Smith, Warsaw; David C. Kelman, Winona Lake, both of Ind.

[73] Assignee: Boehringer Mannheim Corporation, Indianapolis, Ind.

[21] Appl. No.: 503,121

[22] Filed: Mar. 30, 1990

Related U.S. Application Data

[63] Continuation of Ser. No. 391,660, Aug. 8, 1989, abandoned, which is a continuation of Ser. No. 238,913, Aug. 31, 1988, abandoned.

[51] Int. Cl.$^5$ ............................................... A61F 2/34
[52] U.S. Cl. ........................................ 623/23; 623/18
[58] Field of Search .................. 623/16, 17, 18, 19, 623/20, 21, 22, 23, 66

[56] References Cited

U.S. PATENT DOCUMENTS

| | | | |
|---|---|---|---|
| 3,623,164 | 11/1971 | Bokros | 623/16 |
| 3,740,769 | 6/1973 | Haboush | 3/1 |
| 3,859,669 | 1/1975 | Shersher | 3/1 |
| 3,906,550 | 9/1975 | Rostoker et al. | 623/16 |
| 3,965,490 | 6/1976 | Murray et al. | 623/16 |
| 4,261,063 | 1/1981 | Blanquaert | 3/1 |
| 4,404,693 | 9/1983 | Zweymuller | 623/23 |
| 4,536,894 | 8/1985 | Galante et al. | 623/18 |
| 4,546,501 | 10/1985 | Gustilo et al. | 623/18 |
| 4,619,659 | 10/1986 | Witzel | 623/18 |
| 4,661,112 | 4/1987 | Muller | 623/18 |
| 4,714,470 | 12/1987 | Webb, Jr. et al. | 623/18 |

FOREIGN PATENT DOCUMENTS

| | | |
|---|---|---|
| 2247721 | 4/1974 | Fed. Rep. of Germany . |
| 2305441 | 8/1974 | Fed. Rep. of Germany . |
| 2438469 | 5/1980 | France . |
| 0158534 | 10/1985 | United Kingdom . |
| 0216489 | 4/1987 | United Kingdom . |

OTHER PUBLICATIONS

"Effect of Femoral Component Section Modulus on the Stress Distribution in the Proximal Human Femur", 8 pages, John A. Engelhardt, Med. & Biol. Eng. & Comput.

Primary Examiner—David J. Isabella
Attorney, Agent, or Firm—Perman & Green

[57] ABSTRACT

A controlled stiffness elongated implant for use in the hip or other appropriate body joint. In the instance of the hip, a ball member fixed to the femur is rotatably engaged with a cup-shaped socket member fixed to the acetabulum of the pelvic bone. The ball member is mounted on one end of a femoral component which has an elongated stem receivable in the intramedullary canal of the femur. The stem has a generally longitudinally directed reduced mid-stem section. The dimension of the reduced mid-stem section is uniform or variable between the proximal and distal ends so as to affect the mass moment of inertia at any given location along the length of said stem to thereby achieve an optimal stem flexibility.

22 Claims, 3 Drawing Sheets

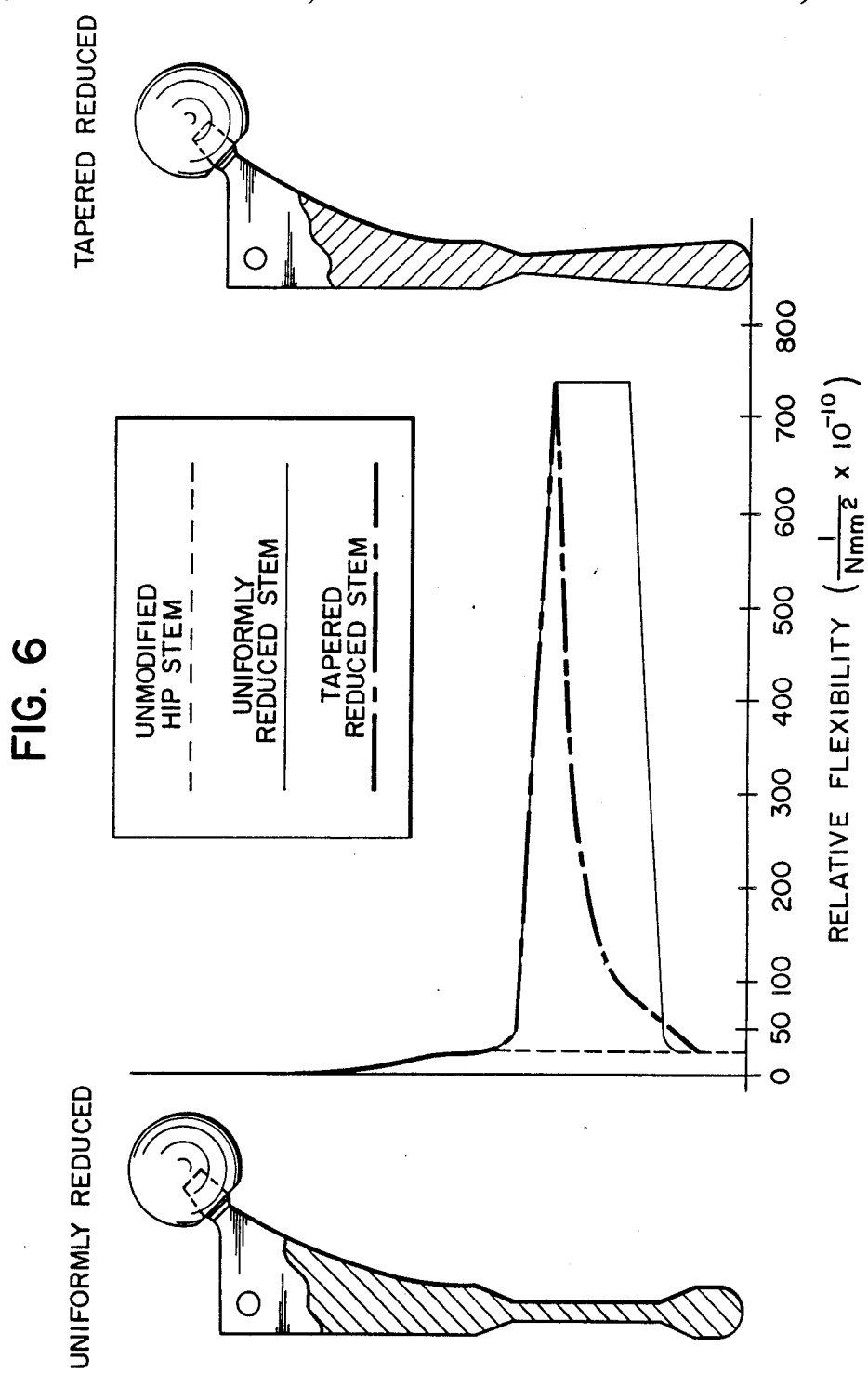

LOAD SHARING FEMORAL HIP IMPLANT

This is a continuation of copending application Ser. No. 07/391,660 filed on Aug. 8, 1989, now abandoned which is a continuation of copending application Ser. No. 238,913 filed on Aug. 31, 1988, now abandoned.

BACKGROUND OF THE INVENTION

I. Field of the Invention

The present invention relates generally to a femoral hip prosthesis and, more particularly, to a femoral component which can be stress tailored to optimally share the load with the femur in which it is implanted.

II. Description of the Prior Art

Based on the precepts of Wolff's Law which states that bone tissue will remodel in direct relation to the stress applied to it, it is desirable to stress bone at an optimal level to minimize and control remodeling after THR (total hip replacement) arthroplasty. Usually some degree of proximal femur bone remodeling accompanies total hip replacement. Due to mechanical stiffness, metallic implants typically stress protect the proximal bone to some extent. In patients with relatively large intramedullary canals which require a large diameter implant for optimal fit, stress protection may be particularly troublesome. In the most extreme case, the proximal femoral bone may resorb to a small fraction of its original mass, possibly causing a loss of support of the implant or implant breakage. It is unfortunate that implant flexural stiffness increases at an exponential rate, typically at powers between two and four, depending upon implant geometry, relative to linear increases in implant dimension. Further aggravating the situation is the fact that there is little correlation between the size of the patient and the diameter of the intramedullary canal. That is, a small, relatively light person may have a femur with a large diameter canal and a much larger person may have a femur with a smaller diameter canal. Therefore, it is desirable to produce an implant, especially a larger diameter implant, with greatly reduced stiffness in relation to its mass.

This can be accomplished in several ways. For example the use of materials which are inherently less stiff, that is, possess a lower flexural modulus might be considered. Thus, the use of titanium alloy or a carbon fiber reinforced polymer composite in lieu of the stiffer cobalt-chrome alloy might be considered. An implant can also be hollowed out. This method is marginally effective, however, due to the fact that the centrally located material contributes little to the stiffness of the implant. For example, if an implant with a round stem of 16 mm diameter is hollowed to a wall thickness of only 2 mm, the resulting decrease in flexural stiffness is only 32% while the decrease in mass is 56%. Interestingly, a 16 mm diameter stem is 6.5 times stiffer than the 10 mm diameter stem. Morscher and Dick reported on nine years of clinical experience with a so-called "isoelastic" shaft prosthesis manufactured using polyacetal resin to transmit forces from the pelvis through the femoral head and neck into the femur in their paper: "Cementless Fixation of 'Isoelastic' Hip Endoprostheses Manufactured from Plastic Materials", *Clinical Orthopaedics*, June, 1983, Volume 176, pages 77–87. They stated: "The optimal fixation of an implant depends mainly on its design and material. The insertion of an artificial joint induces remodeling of the bony structures. If stability is not achieved, the implant sooner or later will loosen. The elasticity, and consequently the deformation, of an implant depend on the elastic modulus of the material and on the prosthetic design. By adjusting the physical characteristics of the foreign material to that of the bone tissue, as well as the design of the prosthesis to the femoral shaft, the entire system would have the same elasticity as a normal femur. A more elastic hip endoprosthesis also may act as a shock absorber during walking, particularly in the heel/strike and toe/off phases."

They proceeded to explain that this was the concept of the "isoelastic" hip endoprosthesis manufactured by Robert Mathys and implanted in 1973. In this instance, the prosthesis was composed of polyacetal resin which has an elasticity modulus approaching that of bone tissue, good durability, and tenacity for highly stressed components in combination with good tissue tolerance. To achieve the acquired structural strength in the neck portion, the component was reinforced by a metallic core that was tapered toward the tip to increase the elasticity of the stem, thereby allowing the stem of the prosthesis to follow the deformation of the bone. In commenting on the design, the authors further stated: "Isoelasticity implies the optimum approximation of the physical characteristics of an implant to those of the bone. An ideal isoelasticity, however, can never be achieved, since bone is anisotropic and the alloplastic materials used for joint arthroplasty show isotropic properties. In addition, there is no adaptation of the structures to the forces acting on the hip, as in the case in viable bone. Moreover, the variety of individual forms and strengths of human bone can never be imitated by an artificial joint. Use of more elastic materials, however, should avoid the disadvantages of the rigid materials used to date."

U.S. Pat. No. 4,287,617 to Tornier discloses a hip prosthesis with a femoral stem which provides a measure of the elasticity spoken of by Morscher and Dick. A transverse section of the Tornier stem is in the form of a substantially rectangular tube of which one of the small sides is virtually cut away so as to leave a very large slot. The C-shaped section thus obtained is said to exhibit excellent transverse elasticity which facilitates the positioning of the pin in the medullary cavity by insertion. Other stated advantages are that the pin is not as heavy as solid designs, and that the cavity encourages bone growth.

An alternate approach to the foregoing is the subject of commonly assigned U.S. application Ser. No. 151,627 to co-inventor Todd S. Smith entitled "Controlled Stiffness Femoral Hip Implant". In that construction, the medial side of the length of the implant is milled out to form a channel shaped stem cross section. The amount of material removed determines the resulting decrease in stiffness of the implant while the outside geometry remains substantially unchanged with the exception of the open channel on the medial side of the implant. The resulting longitudinal channel lies generally in the coronal plane when the stem is in the implanted condition. The depth of the channel is variable between the proximal and distal ends of the femoral implant so as to affect the mass moment of inertia at any given location along a length of the stem to thereby achieve an optimal stem flexibility. That is, the stem is so formed that at specified locations along its length, it substantially correlates to the flexibility of the femur itself.

SUMMARY OF THE INVENTION

Yet another alternative approach to the foregoing is the subject of this disclosure. Briefly stated, the central portion of the length of the implant is machined to reduce its outside dimension such that it has a smaller cross section. The amount of material removed determines the resulting decrease in stiffness of the implant.

Because of the reduction of the moment of inertia of the implant stem, it is more flexible. It also experiences higher stem stresses upon loading of the implant due to its reduced section size. Therefore, a careful balance must be achieved between the amount of material removed from the stem and the expected stress levels expected by the particular size implant.

The material removed from the periphery of the mid-stem region of the implant may be in a uniform fashion or preferentially. The amount of material comprising the reduced section of the implant may be variable between the proximal and distal ends of the femoral implant so as to affect the mass moment of inertia at any given location along a length of the stem to thereby achieve an optimal stem flexibility. That is, the stem is so formed that at specified locations along its length, it may substantially correlate to the flexibility of the femur itself.

However, it is desirable that when the mid-stem section is formed, the resultant dimension of the mid-stem be no smaller than 25% of the original cross sectional dimension assuming the cross sectional shape is approximately round. Reasons supporting this desirable relationship include the fact that the stem may otherwise deform due to impact forces needed to insert the implant into the femur. Indeed, to preclude this potential difficulty, it is preferable that the final cross sectional area will be no less than 25% of the dimension of a comparable full sized non-contoured implant stem.

The femoral stem exhibiting the qualities of the invention may be composed of any of the common materials generally employed for implants including titanium, titanium alloy, cobalt-chromium alloy, and composite materials. However, the use of ceramics and sintered powdered metal constructions may also be considered.

The reduced mid-stem section itself may be formed during a molding process or by mechanical or chemical milling procedures, or in any other suitable fashion.

Also, according to the invention, it is considered that there would be a standard size range of stems, perhaps seven to ten different sizes varying in outer diameter, length, dimension of the reduced mid-stem section, the amount of the taper from the proximal to the distal ends of the stem. The closest sizes would be determined radiographically prior to surgery, although the final size decided upon for implanting could be finally chosen during surgery.

Other and further features, objects, advantages, and benefits of the invention will become apparent from the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention and, together with the description, serve to explain the principles of the invention in general terms. Like numerals refer to like parts throughout the disclosure.

BRIEF DESCRIPTION OF THE DRAWINGS

FIG. 6 is a graph illustrating the relative flexibility of the series of femoral components which were presented in FIG. 5.

DETAILED DESCRIPTION OF THE PREFERRED EMBODIMENT

Figure 1:
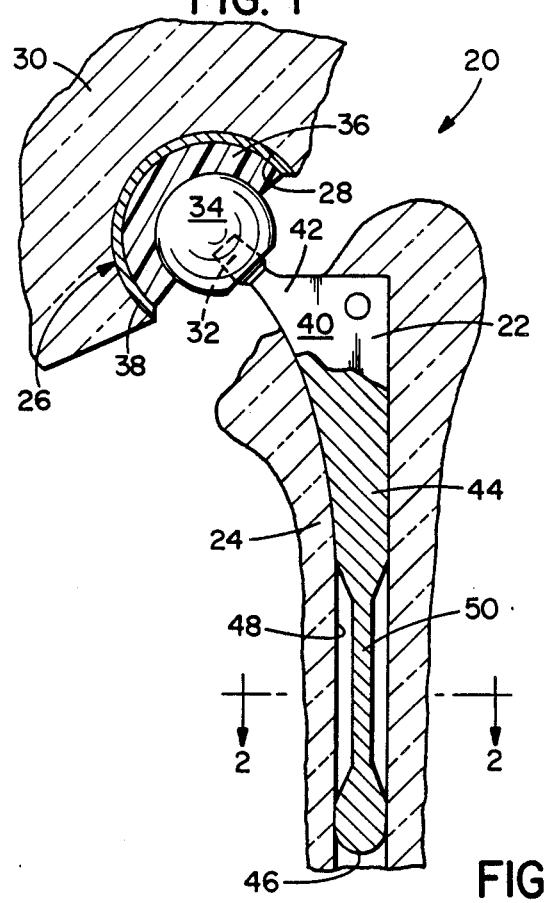
FIG. 1 is a side elevation view, certain parts being cut away and shown in section, of a hip prosthesis, including a femoral component embodying the invention.

Turn now to the drawings, and initially to FIG. 1, which illustrates a hip prosthesis 20 which embodies the invention. As illustrated, a femoral component 22 is suitably implanted in the femur 24 and is cooperatively engaged with an acetabular component 26. The latter component is suitably implanted in the acetabulum 28 of the pelvis 30. In customary fashion, the femoral component 22 has a taper 32 at its extreme proximal end adapted to fittingly receive thereon a ball 34. In turn, the ball is rotatably engaged with a bearing 36 of the acetabular component 26 which may be supported in a metal cup 38 which is generally fixed to the pelvis 30. The femoral component 22 further includes a shoulder 40, with the taper 32 being joined to the shoulder via a neck 42. A stem 44 extends away from the shoulder 40 to a distal or tip end 46.

Figure 2:
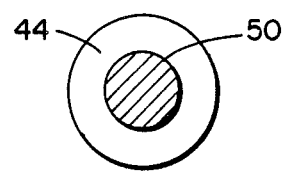
FIG. 2 is a cross section view taken generally along line 2—2 in FIG. 1.
Figure 2A:
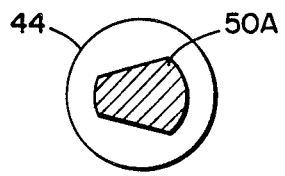

In a customary manner, the stem 44 is received in the intramedullary canal 48 of the femur 24. Stem 44 is formed with a reduced mid-section 50 which lies generally in the coronal plane of the body of the person in whom the prosthesis is implanted. The dimensions of the reduced mid section 50 (see especially FIG. 2) may be variable between the proximal and distal ends of the femoral component 22, its purpose being to affect the mass moment of inertia of the femoral component at any given location along the length of the stem 44 to thereby achieve an optimal stem flexibility. The shape of the cross section 50 may also vary, including asymmetrical shapes, as desired, in order to achieve optimal stem flexibility. A stem cross section as indicated at 50A in FIG. 2A is generally representative of such a modified shape.

Figure 3:
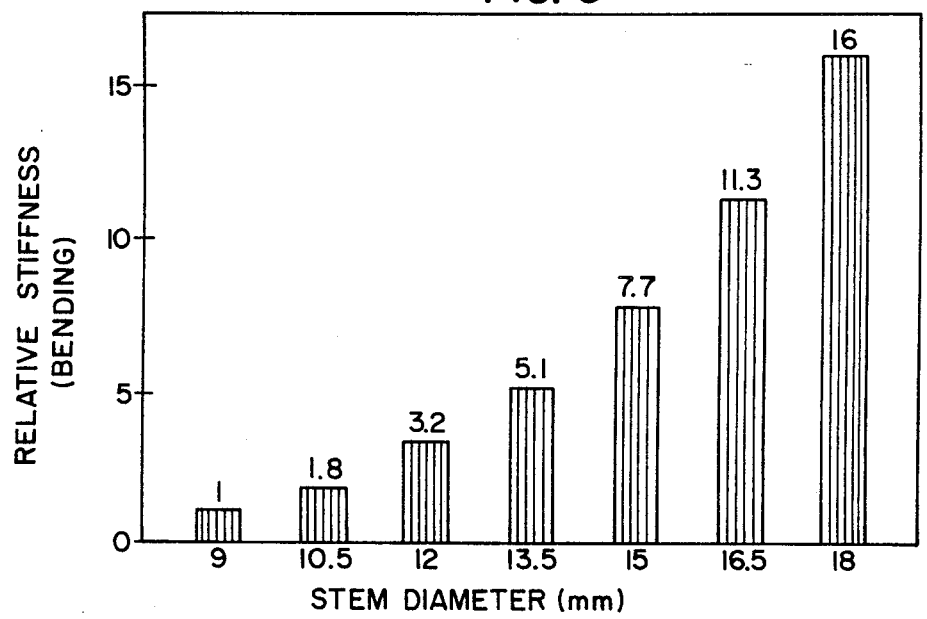
FIG. 3 is a bar graph indicating relative stiffness of a series of stems of varying diameters for femoral components which are currently available commercially.

It was previously mentioned as being unfortunate that implant flexural stiffness increases at an exponential rate, typically at powers between two and four, depending upon implant geometry, relative to linear increases in implant dimension. Graphic proof of this statement is presented in FIG. 3 which is a bar graph indicating relative stiffness of a series of stems of varying diameters which are currently available for implanting. It is noteworthy that the 18 millimeter diameter stem exhibits 16 times the stiffness of the 9 millimeter diameter stem. The invention serves to avoid this exponential increase and limits the increase in stiffness to an approximately linear relationship with increasing stem diameter.

It will be appreciated that femoral hip implants are subjected predominately to a bending mode of loading based on biomechanical analyses. This loading give rise to the highest stem stresses according to the formula:

$$S_{max} = Mc/I$$

where $S_{max}$ is the maximum stress at any location of interest along the stem; M is the bending moment imparted to the structure at the particular location of interest; c is the distance form the neutral axis to the location of interest; and I is the mass moment of inertia, a geometrical consideration.

If the maximum allowable stress based on material limitations is known and if the loading condition of the implant based on biomechanical analyses is known, one can then solve for the necessary moment of inertia via the rearrangement of the above equation, as follows:

$$I = Mc/S_{max}$$

The cross-sectional area of the reduced mid-stem section shall not be less than 25% of the unmodified stem cross-sectional area, which is to say that the original cross-sectional area shall not be reduced by more than 75%, so that the forces required to introduce the implant into the femur do not deform the implant.

Furthermore, stiffness of the desired implant at any given location along its length is a known quantity. This is determined from clinical experience. Stiffness is proportional to the moment of inertia, I, and therefore increases in proportion to the fourth power of the diameter of the stem. However, according to the invention, this increase would be limited to a fraction of what it would be for a solid implant and this fractional increase is achieved by means of the reduced mid-stem section.

Figure 4:
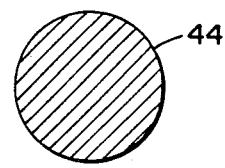
FIG. 4 is a cross section view of the stem of a femoral component having a circular cross section and awaiting modification according to the invention.

With the aid of FIG. 4, it should be clear that $$I_{\text{implant w/reduced section}} = I_{\text{circle}} - I_{\text{reduced section}}$$

Thus, $I_{\text{implant w/reduced section}}$ is determined for various reduced section dimensions used to satisfy the aforementioned equation, namely:

$$S_{max} = Mc/I$$

Figure 5:
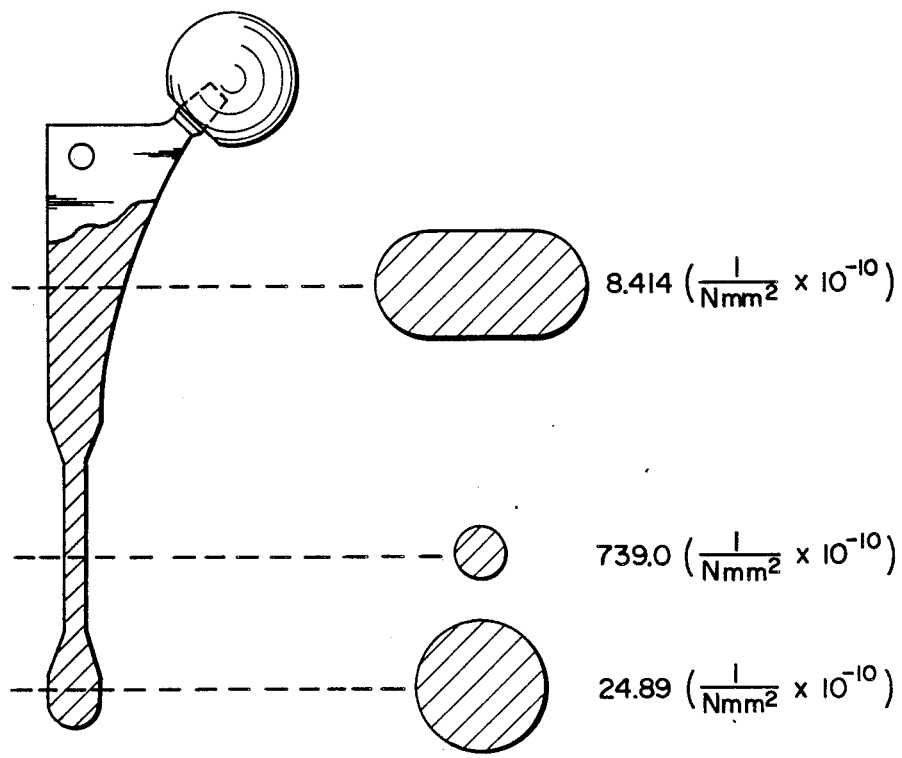
FIG. 5 is, in part, a schematic side elevation view, partly in section, of a femoral component embodying the invention and, in part, a graph presenting the section properties at various locations on the implant.

As was previously explained, the primary thrust of the invention is to prevent stress shielding at the proximal end of the femur 24 and, toward this end, to impart more stress and more strain into the femur. This desired result has been achieved as is seen in FIG. 5 which is illustrative of the relative flexibility of the test implant 58 at three of the cross sectional locations presented in the FIG. 6 graph.

While various embodiments of the invention have been disclosed in detail, it should be understood by those skilled in the art that various other modifications may be made to the illustrated embodiments without departing from the scope of the invention as described in the specification and defined in the appended claims.

What is claimed is:

1. A component of an artificial joint for replacing a damaged natural joint in a skeletal structure of a body which includes a prosthesis having a first cooperating member secured to a first, long, bone having an intramedullary canal and a second cooperating member secured either to a second bone or being a natural part of the second bone, the first and second cooperating members being interengaging and relatively movable to permit relative movement between the first and second bones, said component comprising:
   an elongated stem having a longitudinal axis lying generally in a coronal plane and said stem configured to be implanted into the intramedullary canal of the first bone; and
   said stem defining proximal, intermediate and distal segments, each segment having a predetermined length terminating at respective proximal and distal ends, said proximal end of the proximal segment being integral with said first cooperating member and said distal end of the distal segment defining a terminal end of the stem;
   said distal end of the proximal segment and the proximal end of the distal segment being directly adjacent to and forming a tapered junction with said proximal and distal ends of the intermediate segment, respectively; and
   wherein the cross-sectional area of the intermediate segment is uniform and reduced over the length thereof up to 75% of the cross-sectional area of a comparable non-contoured stem to thereby affect the mass moment of inertia at any given location along the length of the stem and thereby achieve an optimal stem flexibility.

2. A component as set forth in claim 1 wherein said mid-stem section is symmetrical in cross section.

3. A component as set forth in claim 1 wherein said mid-stem section is asymmetrical in cross-section.

4. A component as set forth in claim 1 wherein said mid-stem section is tapered along the longitudinal axis.

5. A component as set forth in claim 1 wherein said mid-stem section is substantially uniform in cross section along the length thereof.

6. A component as set forth in claim 1 wherein said mid-stem section is variable in cross section along the length thereof.

7. A component as set forth in claim 1 which is composed of any one of titanium, titanium alloy, cobalt-chromium alloy, and composite materials.

8. In an artificial joint for replacing a damaged natural joint in a skeletal structure of a body which includes a prosthesis having a first cooperating member secured to a first, long, bone having an intramedullary canal and a second cooperating member either secured to a second bone or being a natural part of the second bone, said first and second cooperating members being interengaging and relatively movable to permit relative movement between the first and second bones, the improvement comprising:
   an elongated stem having a longitudinal axis lying generally in a coronal plane and said stem configured to be implanted into the intramedullary canal of the first bone; and
   said stem defining proximal, intermediate and distal segments, each segment having a predetermined length terminating at respective proximal and distal ends, said proximal end of the proximal segment being integral with said first cooperating member and said distal end of the distal segment defining a terminal end of the stem;

said distal end of the proximal segment and the proximal end of the distal segment being directly adjacent to and forming a tapered junction with said proximal and distal ends of the intermediate segment, respectively; and wherein the cross-sectional area of the intermediate segment is uniform and reduced over the length thereof up to 75% of the cross-sectional area of a comparable non-contoured stem to thereby affect the mass moment of inertia at any given location along the length of the stem and thereby achieve an optimal stem flexibility.

9. The improvement as set forth in claim 8 wherein said mid-stem section is symmetrical in cross-section.

10. The improvement as set forth in claim 8 wherein said mid-stem section is asymmetrical in cross-section.

11. The improvement as set forth in claim 8 wherein said mid-stem section is tapered along the longitudinal axis.

12. The improvement as set forth in claim 8 wherein said mid-stem section is substantially uniform in cross section along the length thereof.

13. The improvement as set forth in claim 8 wherein said mid-stem section is variable in cross section along the length thereof.

14. The improvement as set forth in claim 8 wherein said stem is composed of any one of titanium, titanium alloy, cobalt-chromium alloy, and composite materials.

15. An artificial joint for replacing a damaged natural joint in a skeletal structure of a body comprising:
   a cup shaped socket member fixed to a first bone of the joint;
   a ball member rotatably engageable with said socket member;
   a mounting member including an elongated stem for securing said ball member to a second bone separate from the first bone, being a long bone with an intramedullary canal, said stem having a longitudinal axis lying generally in a coronal plane and configured to be implanted into the intramedullary canal of the second bone, said stem defining proximal, intermediate and distal segments, each segment having a predetermined length terminating at respective proximal and distal ends, said proximal end of the proximal segment being integral with said ball member and said distal end of the distal segment defining a terminal end of the stem;
   said distal end of the proximal segment and the proximal end of the distal segment being directly adjacent to and forming a tapered junction with said proximal and distal ends of the intermediate segment, respectively; and
   wherein the cross-sectional area of the intermediate segment is uniform and reduced over the length thereof up to 75% of the cross-sectional area of a comparable non-contoured stem to thereby affect the mass moment of inertia at any given location along the length of said stem and thereby achieve an optimal stem flexibility.

16. An artificial joint as set forth in claim 15 wherein said mid-stem section is symmetrical in cross section.

17. An artificial joint as set forth in claim 15 wherein said mid-stem section is asymmetrical in cross-section.

18. An artificial joint as set forth in claim 15 wherein said mid-stem section is tapered along the longitudinal axis.

19. An artificial joint as set forth in claim 15 wherein said mid-stem section is substantially uniform in cross section along the length thereof.

20. An artificial joint as set forth in claim 15 wherein said mid-stem section is variable in cross section along the length thereof.

21. An artificial joint as set forth in claim 15 including: a femoral component of a hip prosthesis for a natural joint in which the first bone is the pelvis and the second bone is the femur, said ball member and said stem being parts of said femoral component.

22. An artificial joint as set forth in claim 7 wherein said mounting member and said ball member are composed of any one of titanium, titanium alloy, cobalt-chromium alloy, and composite materials.

* * * * *